United States Patent
Keacher et al.

(10) Patent No.: US 7,774,067 B2
(45) Date of Patent: Aug. 10, 2010

(54) AUTOGENERATION OF NEUROSTIMULATION THERAPY PROGRAM GROUPS

(75) Inventors: Jeffrey T. Keacher, St. Paul, MN (US); Steven M. Goetz, Brooklyn Center, MN (US); Andrew H. Houchins, Lino Lakes, MN (US); Theodore J. Stone, St. Louis Park, MN (US); Donald R. Johnson, Lino Lakes, MN (US); Shyam Gokaldas, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 297 days.

(21) Appl. No.: 11/402,652

(22) Filed: Apr. 12, 2006

(65) Prior Publication Data

US 2007/0244519 A1 Oct. 18, 2007

(51) Int. Cl.
*A61N 1/08* (2006.01)
(52) U.S. Cl. .......................................... 607/48; 607/46
(58) Field of Classification Search .................. 600/300; 607/2, 19, 28, 31, 48, 57
See application file for complete search history.

(56) References Cited

U.S. PATENT DOCUMENTS

| | | | |
|---|---|---|---|
| 4,515,158 A | 5/1985 | Patrick et al. | |
| 4,549,548 A | 10/1985 | Wittkampf et al. | |
| 5,033,469 A | 7/1991 | Brodard | |
| 5,775,331 A | 7/1998 | Raymond et al. | |
| 5,893,883 A | 4/1999 | Torgerson et al. | |
| 5,938,690 A | 8/1999 | Law et al. | |
| 6,044,303 A | 3/2000 | Agarwala et al. | |
| 6,052,624 A | 4/2000 | Mann | |
| 6,234,964 B1 * | 5/2001 | Iliff ........................... | 600/300 |
| 6,393,325 B1 | 5/2002 | Mann et al. | |

(Continued)

FOREIGN PATENT DOCUMENTS

EP  0 730 882  9/1996

(Continued)

OTHER PUBLICATIONS

U.S. Appl. No. 11/402,657, filed Apr. 12, 2006 entitled Rule-Based Stimulation Program Search by Steven M. Goetz et al.

(Continued)

*Primary Examiner*—Carl H Layno
*Assistant Examiner*—Luther G Behringer
(74) *Attorney, Agent, or Firm*—Shumaker & Sieffert, P.A.

(57) ABSTRACT

Techniques for automatically generating neurostimulation therapy program groups are disclosed. The techniques may include receiving rating information and information describing actual therapy effects for a plurality of tested programs, and receiving target therapy data describing target therapy effects. The techniques may include automatically generating plurality of program groups based on the rating information and a comparison of actual effects to the target therapy effects. Actual effects and target therapy effects may be, for example, actual paresthesia areas and target paresthesia areas. The techniques may also include determining whether a sufficient number of programs have been tested to generate a desired number of programs groups and, if a sufficient number have not been tested, automatically generating additional programs based on the tested programs, and automatically generating program groups from the tested and automatically generated programs.

34 Claims, 7 Drawing Sheets

U.S. PATENT DOCUMENTS

| | | | |
|---|---|---|---|
| 6,440,090 | B1 | 8/2002 | Schallhorn |
| 6,473,653 | B1 | 10/2002 | Schallhorn et al. |
| 6,480,743 | B1 | 11/2002 | Kirkpatrick et al. |
| 6,516,227 | B1 * | 2/2003 | Meadows et al. ............. 607/46 |
| 6,587,724 | B2 | 7/2003 | Mann |
| 6,622,048 | B1 * | 9/2003 | Mann et al. .................... 607/46 |
| 7,146,223 | B1 * | 12/2006 | King ........................... 607/117 |
| 7,313,440 | B2 * | 12/2007 | Miesel ......................... 607/19 |
| 2001/0049542 | A1 * | 12/2001 | Florio et al. ................... 607/28 |
| 2002/0035384 | A1 * | 3/2002 | Fox et al. ....................... 607/31 |
| 2002/0116036 | A1 | 8/2002 | Daignault, Jr. et al. |
| 2002/0169484 | A1 | 11/2002 | Mathis et al. |
| 2003/0004549 | A1 | 1/2003 | Hill et al. |
| 2003/0036783 | A1 * | 2/2003 | Bauhahn et al. ............... 607/59 |
| 2004/0041352 | A1 | 3/2004 | Hohe et al. |
| 2004/0106958 | A1 | 6/2004 | Mathis et al. |
| 2004/0158298 | A1 | 8/2004 | Gliner et al. |
| 2004/0181262 | A1 * | 9/2004 | Bauhahn ...................... 607/48 |
| 2004/0215288 | A1 * | 10/2004 | Lee et al. ...................... 607/48 |
| 2004/0267330 | A1 * | 12/2004 | Lee et al. ...................... 607/48 |
| 2005/0060009 | A1 * | 3/2005 | Goetz .......................... 607/48 |

FOREIGN PATENT DOCUMENTS

| | | |
|---|---|---|
| EP | 1 249 254 | 10/2002 |
| EP | 1 304 137 | 4/2003 |
| WO | WO 01/83028 | 11/2001 |
| WO | WO 01/93953 | 12/2001 |
| WO | WO 02/09808 | 2/2002 |
| WO | WO 2004/041352 | 5/2004 |
| WO | WO 2007/117348 | * 10/2007 |

OTHER PUBLICATIONS

Litt et al., "Translating Seizure Detection, Prediction and Brain Stimulation Into Implantable Devices for Epilepsy," Proceedings of the 1$^{st}$ International IEEE EMBS, Conference on Neural Engineering Capri Island, Italy, Mar. 20-22, 2003, pp. 485-488.

D'Alessandro et al., "A Genetic Approach to Selecting the Optimal Feature for Epileptic Seizure Prediction," 2001 Proceedings of the 23$^{rd}$ Annual EMBS International Conference, Istanbul, Turkey, Oct. 25-28, 2001, pp. 1703-1706.

International Search Report and Written Opinion dated Jul. 27, 2007 for corresponding PCT Application Serial No. PCT/US2007/002285 (10 pgs).

Notification of Transmittal of the International Preliminary Report on Patentability dated Jul. 15, 2008 for corresponding PCT Application Serial No. PCT/US2007/002285 (6 pgs).

* cited by examiner

AUTOGENERATION OF NEUROSTIMULATION THERAPY PROGRAM GROUPS

TECHNICAL FIELD

The invention relates to medical devices, and more particularly, to programming of medical devices that deliver neurostimulation therapy.

BACKGROUND

Medical devices are used to deliver neurostimulation therapy to patients to treat a variety of symptoms or conditions such as chronic pain, tremor, Parkinson's disease, epilepsy, incontinence, or gastroparesis. Typically, medical devices deliver neurostimulation therapy in the form of electrical pulses via leads that include electrodes. To treat the above-identified symptoms or conditions, for example, the electrodes may be located proximate to the spinal cord, peripheral nerves, pelvic nerves, or stomach, or within the brain of a patient. The electrodes carried on one or more leads that are implanted within a patient may be referred to as an electrode set or array.

A clinician may select values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an electrode set to be used to deliver the pulses, e.g., a combination of electrodes from the electrode set. A combination of electrodes may be defined by the polarities, e.g., positive, negative, or off (high impedance), of each of the electrodes within the electrode set. A group of parameter values may be referred to as a program in the sense that they drive the neurostimulation therapy to be delivered to the patient.

In some cases, a medical device delivers neurostimulation therapy according to a group of two ore more programs, i.e., a program group. The medical device may alternate delivery of neurostimulation therapy pulses according to the various programs of a program group at a rate such that the patient does not perceive transitions between the programs. For example, the medical device may deliver each neurostimulation therapy pulse according to a different one of the plurality of programs of a program group, or may deliver a plurality of pulses according to one of the programs before switching to another of the programs of the program group. The constituent programs of a program group may address different symptoms, allowing the program group as a whole to more completely address the symptoms of a patient. For example, the constituent programs of a program group may address different regions of pain, allowing the group as whole to address a complex pain pattern.

The process of selecting values for the parameters that provide adequate therapeutic results can be time consuming, and may require a great deal of trial and error before one or more preferred programs are discovered. The preferred programs may be programs that are better in terms of clinical efficacy versus side effects experienced and power consumption than other programs tested. Where a medical device delivers neurostimulation therapy according to program groups, the process of manually assembling preferred programs into groups may further increase the amount of time and effort required for a therapy programming session. For example, manual assembly of programs into groups may require a clinician to recall from memory or handwritten notes the efficacy of a plurality of programs, as well as, for example, the locations at which the patient experiences pain, and at which the patient experienced the paresthesia produced by the various programs.

SUMMARY

In general, the invention is directed to techniques for automatically generating neurostimulation therapy program groups. Each of the program groups includes a plurality or subset of neurostimulation therapy programs tested on a patient, e.g., during a programming session. The techniques of the invention may allow a clinician or patient to more quickly and easily identify preferable program groups during a programming session. The techniques of the invention may also allow the patient to be more readily provided with a greater number and variety of program groups, which the patient may evaluate at home, reducing the amount of time in a clinic setting required to identify preferable program groups for the patient.

The techniques may include receiving rating information and information describing actual therapy effects for a plurality of tested programs, and receiving target therapy data describing target therapy effects. The techniques may include automatically generating plurality of program groups based on the rating information and a comparison of actual effects to the target therapy effects. Actual effects and target therapy effects may be, for example, actual paresthesia areas and target paresthesia areas.

Automatically generating a plurality of program groups may include selecting one or more programs such that the actual effects of the one or more programs substantially match the target therapy effects. For example, if the target therapy information indicates that program groups producing paresthesia in the left leg and lower back are desired, a programming device may select one or more programs that result in paresthesia in one or both of the left leg and lower back. Further, the programs may be selected based on their rating information, e.g., higher rated programs may be selected before lower rated programs.

In some embodiments, the programming device may sort a plurality of tested programs into a plurality of lists based on the actual effects. For example, a programming device according to the invention may sort programs that resulted in paresthesia at different areas of the body of the patient into different lists. The programming device may then rank the programs within each of the lists according to the rating information, select programs from the lists as needed to match the actual effects to the target therapy effects based on the rankings, and assemble the selected programs into the plurality of program groups.

For example, if the target therapy information indicates that program groups producing paresthesia in the left leg and lower back are desired, the programming device may select programs from two lists that include programs that produce paresthesia in the left leg and lower back, respectively. The programming device may select programs according to the rankings of the lists, e.g., select higher ranked programs first, and assemble the selected programs into groups. Each automatically generated program group may have at least one program from each of the lists, and any number of program groups desired by a user may be automatically generated.

In other embodiments, a programming device may combinatorially generate program groups from the tested programs, and then select the number of program groups desired by a user from among the combinatorially generated groups. The programming device may apply an algorithm to each of the program groups, which may provide a score for each of the program groups based on at least one of the rating information for the constituent programs of the program groups or a comparison of the actual effects for the constituent programs to the target therapy effects. The programming device may select the desired number of program groups from among the combinatorially generated groups based on the scores, e.g., select the "best" N program groups as indicated by the scores.

In some embodiments, a user, such as a clinician, may indicate a desired number of program groups, and the programming device may automatically generate the desired number of program groups. A programming device may determine whether there is a sufficient number of programs available to generate the desired number of programs groups, e.g., whether a sufficient number of programs have been tested during a programming session. If a sufficient number have not been tested, the programming device may automatically generate additional programs based on the tested programs, and automatically generate program groups from the tested and automatically generated programs. The programming device may automatically generate additional programs by, for example, generating copies of tested programs with one or more program parameters, such as electrode configurations, of the copies automatically modified relative to the tested programs.

In one embodiment, the invention is directed to a method comprising receiving target therapy information that describes a plurality of target therapy effects and, for each of a plurality of neurostimulation programs tested on a patient, receiving rating information and information describing at least one actual effect resulting from delivery of neurostimulation therapy according to the program. The method further comprises comparing the actual effects for the tested programs to the target therapy effects, and automatically generating a plurality of program groups based on the rating information and the comparison, each of the program groups including a subset of the neurostimulation programs tested on the patient.

In another embodiment, the invention is directed to a computer-readable medium comprising instructions. The instructions cause a programmable processor to receive target therapy information that describes a plurality of target therapy effects and, for each of a plurality of neurostimulation programs tested on a patient, receive rating information and information describing at least one actual effect resulting from delivery of neurostimulation therapy according to the program. The instructions further cause a programmable processor to compare the actual effects for the tested programs to the target therapy effects, and automatically generate a plurality of program groups based on the rating information and the comparison, each of the program groups including a subset of the neurostimulation programs tested on the patient.

In another embodiment, the invention is directed to a device comprising a user interface and a processor. The processor receives target therapy information that describes a plurality of target therapy effects via the user interface, for each of a plurality of neurostimulation programs tested on a patient, receives rating information and information describing at least one actual effect resulting from delivery of neurostimulation therapy according to the program via the user interface, compares the actual effects for the tested programs to the target therapy effects, and automatically generates a plurality of program groups based on the rating information and the comparison, each of the program groups including a subset of the neurostimulation programs tested on the patient.

In another embodiment, the invention is directed to a device comprising means for receiving target therapy information that describes a plurality of target therapy effects, means for receiving rating information and information describing at least one actual effect resulting from delivery of neurostimulation therapy according to the program for each of a plurality of neurostimulation programs tested on a patient, means for comparing the actual effects for the tested programs to the target therapy effects and means for automatically generating a plurality of program groups based on the rating information and the comparison, each of the program groups including a subset of the neurostimulation programs tested on the patient.

The invention may provide advantages. For example, by automatically generating a plurality of program groups according to the invention, embodiments of the invention may allow a clinician to avoid manual assembly of program groups from tested programs based on memory. Consequently, use of such embodiments may reduce the time required of the clinician and patient to program an implantable medical device for the provision of neurostimulation therapy to the patient, and also reduce the likelihood of clinician error, such as inclusion of less efficacious programs in manually created program groups. The automatically generated program groups may also be more complete, e.g., may more completely address the symptoms of the patient than ones generated by a clinician using an idiosyncratic or trial and error method.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
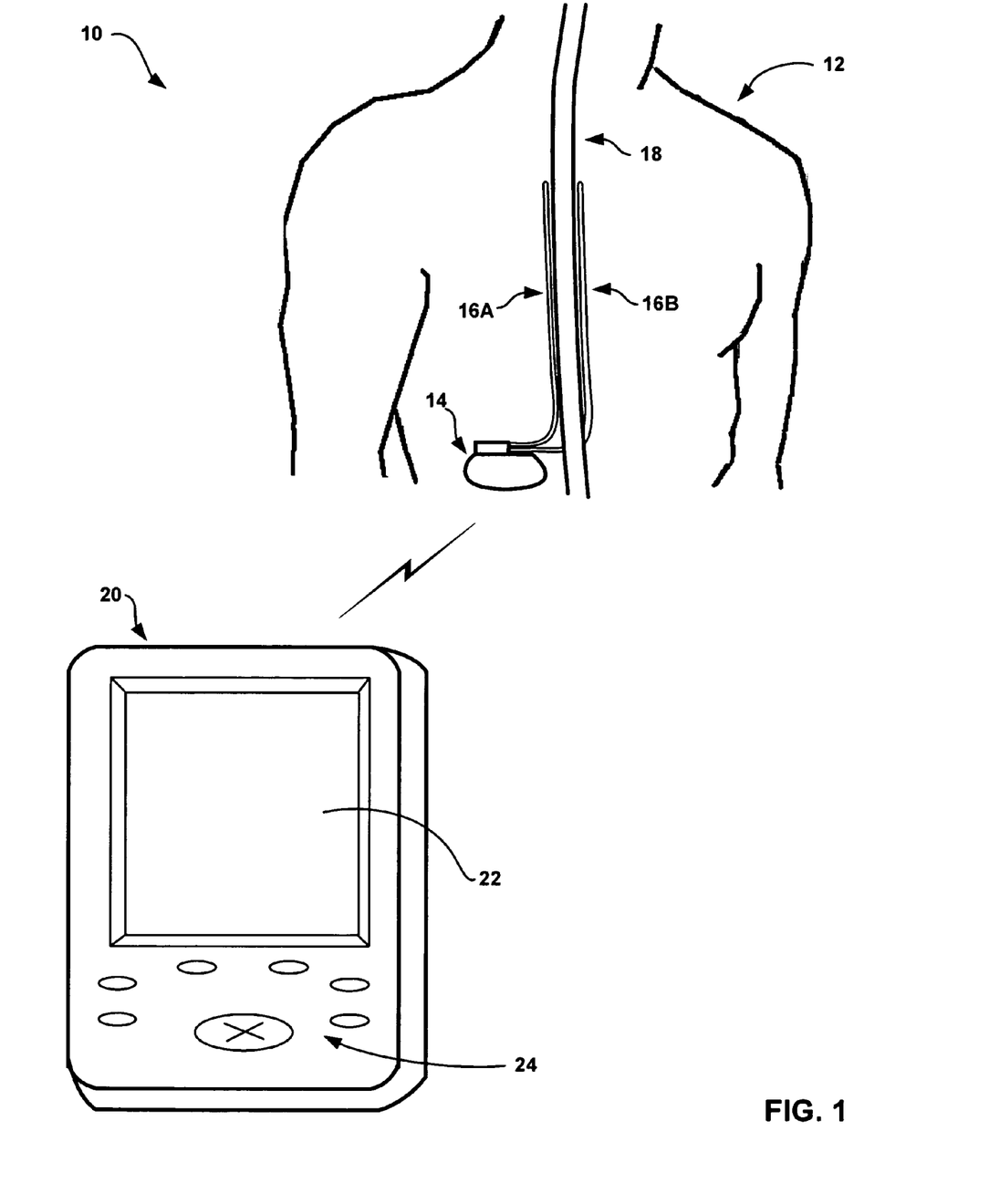
FIG. 1 is a conceptual diagram illustrating an exemplary system for managing delivery of neurostimulation therapy to a patient.

FIG. 1 is a conceptual diagram illustrating an example system 10 for managing delivery of neurostimulation therapy to a patient 12. System 10 includes an implantable medical device (IMD) 14 that delivers neurostimulation therapy to patient 12. In exemplary embodiments, IMD 14 takes the form of an implantable pulse generator, and delivers neurostimulation therapy to patient 12 in the form of electrical pulses.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1, or the delivery of SCS therapy.

IMD 14 may be coupled to any number of leads 16, and the one or more leads 16 may extend from IMD 14 to any position within patient 12 for delivery of neurostimulation to treat any of a number of symptoms or conditions of patient 12. For example, one or more leads 16 may extend from IMD 14 to the brain (not shown) of patient 12, and IMD 14 may deliver deep brain stimulation (DBS) therapy to patient 12 to, for example, treat Parkinson's disease, tremor, epilepsy or psychological disorders. As further examples, one or more leads 16 may be implanted proximate to the pelvic nerves (not shown) or stomach (not shown), and IMD 14 may deliver neurostimulation therapy to treat incontinence or gastroparesis.

Each of leads 16 includes one or more electrodes (not shown). The electrodes carried by leads 16 form a set, i.e., array, of electrodes implanted within patient 12. IMD 14 delivers neurostimulation to patient 12 via a selected combination of the electrodes within the electrode set. A combination of electrodes from within an electrode set includes two or more of the electrodes, and includes at least one anode and at least one cathode. An "electrode configuration" defines the polarities, e.g., positive, negative, or off (high impedance), of each of the electrodes within the electrode set, and thereby defines a combination of electrodes from within an electrode set.

IMD 14 delivers neurostimulation therapy to patient 12 according to a program. The program may include values for a number of parameters, and the parameter values define the neurostimulation therapy delivered according to that program. In embodiments where IMD 14 delivers neurostimulation therapy in the form of electrical pulses, the parameters may include voltage or current pulse amplitudes, pulse widths, pulse rates, and the like. The program also includes an electrode configuration defining polarities of each of the electrodes of the electrode set for delivery of neurostimulation by IMD 14 according to that program.

At any given time, IMD 14 delivers neurostimulation therapy to a patient according to a selected one of a plurality of program groups. A program group may include a single neurostimulation therapy program, but will generally include two or more programs. When delivering neurostimulation according to a program group, IMD 14 may alternate delivery of neurostimulation therapy pulses according to the various programs of the program group at a rate such that the patient does not perceive transitions between the programs. For example, IMD 14 may deliver each neurostimulation therapy pulse according to a different one of the plurality of programs of a program group, or may deliver a plurality of pulses according to one of the programs before switching to another of the programs of the program group. As discussed above, the constituent programs of a program group may address different symptoms, allowing the program group as a whole to more completely address the symptoms of a patient. For example, the constituent programs of a program group may address different regions of pain, allowing the group as whole to address a complex pain pattern.

System 10 also includes a clinician programmer 20. Clinician programmer 20 may, as shown in FIG. 1, be a handheld computing device. In the illustrated example, clinician programmer 20 includes a display 22, such as a LCD or LED display, to display information to a user, and a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician (not shown) may use clinician programmer 20 to program neurostimulation therapy for patient 12. In general, a clinician programs neurostimulation therapy for patient 12 by specifying one or more programs, e.g., by selecting parameter values for one or more programs, to be used by IMD 14 for delivery of neurostimulation to patient 12. A number of programs, each program including an electrode configuration, are tested on patient 12, e.g., clinician programmer 20 directs IMD 14 to deliver neurostimulation therapy to patient 12 according to each program.

In some embodiments, the clinician enters parameters, directs clinician programmer 20 to program IMD 14 with the parameters, and receives feedback from patient 12 for each program tested on patient 12. In other embodiments, clinician programmer 20 provides an automated testing routine for sequentially testing a number of programs on patient 12. For example, after the clinician initializes clinician programmer 20, patient 12 may interact with clinician programmer 20 to control presentation of, and provide feedback for, a number of automatically generated and sequentially presented programs. Exemplary automated testing routines are described in greater detail in U.S. Pat. No. 6,308,102, issued to Sieracki et al.

The feedback received during testing of the individual programs may include rating information, as well as information describing one or more actual effects of the program. The rating information for a program may include one or more numerical values that represent subjective ratings by patient 12 of, for example, efficacy and/or side effects associated with delivery of neurostimulation according to the program. The rating information may also include information describing particular side effects, such as twitching, discomfort or nausea for spinal cord stimulation, or laughter or difficulty speaking for brain stimulation.

Additionally, the rating information may include information relating to power consumption resulting from delivery of stimulation according to the program. Power consumption information may include, for example, an estimation of the impact of delivering stimulation according to the program on a battery of IMD 14, e.g., a current drain rate or battery end of life estimation. As another example, in embodiments in which IMD 14 includes a rechargeable battery, information relating to power consumption may include an estimation of the operational time available between battery rechargings when the program is delivered. The power consumption resulting from delivery of stimulation according to the program may be closely related to the stimulation amplitude required in order to achieve efficacious stimulation for the program, as well as the pulse width and pulse rate.

Rating information may also include an indication of the therapeutic amplitude range for the program, e.g., the range from the amplitude value at which a stimulation effect was first perceived during delivery of stimulation according to the program, to the amplitude value at which stimulation according to the program became intolerable, which may be due to, for example, side-effects. In general, programs with lower power consumption and a greater therapeutic range are preferred. The greater therapeutic range may indicate that patient 12 may increase amplitude to, for example, address changes in symptom intensity or accommodation of the stimulation, without experiencing intolerable side-effects, and without needing to select a different program or visit a clinic for reprogramming of IMD 14. Efficacy, side effects, power consumption and therapeutic range are examples of different "metrics" for rating a program. In general, programmer 20 may record values for a plurality of metrics for each program tested on patient 12 during a programming session.

The one or more actual effects of delivery of stimulation according to the program may be, for example, one or more areas of the body of patient 12 at which the patient experiences paresthesia when stimulation is delivered according to the program. In embodiments in which IMD 14 delivers stimulation to the brain of patient 12, e.g., DBS, the one or more actual effects may be, for example, reduction of tremor or improvement of gait.

As will be described in greater detail below, clinician programmer 20 automatically generates neurostimulation program groups from the tested programs. Clinician programmer 20 may generate the program groups in response to receiving a command from a user, such as a clinician, and may generate a number of program groups indicated by the user. Each of the program groups includes a plurality or subset of neurostimulation therapy programs tested on a patient during a programming session.

Clinician programmer 20 may receive target therapy information from the user describing target therapy effects for the automatically generated program groups and, in some embodiments, a desired number of program groups. The target therapy effects may include one or more areas of the body of patient 12 at which the user desires the automatically generated program groups to produce paresthesia. In other embodiments, the target therapy effects may include one or more symptoms which the user desires the program groups to address, such as tremor. Using any of a variety of techniques, which will be described in greater detail below, clinician programmer 20 automatically generates a plurality of program groups from the tested programs based on the rating information for the tested programs and a comparison of actual effects recorded for the tested to the target therapy effects.

Using the techniques of the invention, clinician programmer 20 may allow a clinician or patient 12 to more quickly and easily identify preferable program groups during a programming session relative to manual assembly of tested programs into program groups. The techniques of the invention may also allow clinician programmer 20 to more readily provide the patient with a greater number and variety of program groups, which the patient may evaluate at home, reducing the amount of time in a clinic setting required to identify preferable program groups for the patient. Use of idiosyncratic or trial and error methods by a clinician to manually assemble program groups from tested programs may also result in clinician error, such as inclusion of less efficacious programs in manually created program groups. Automatic generation of program groups by clinician programmer 20 may avoid such errors.

Figure 2:
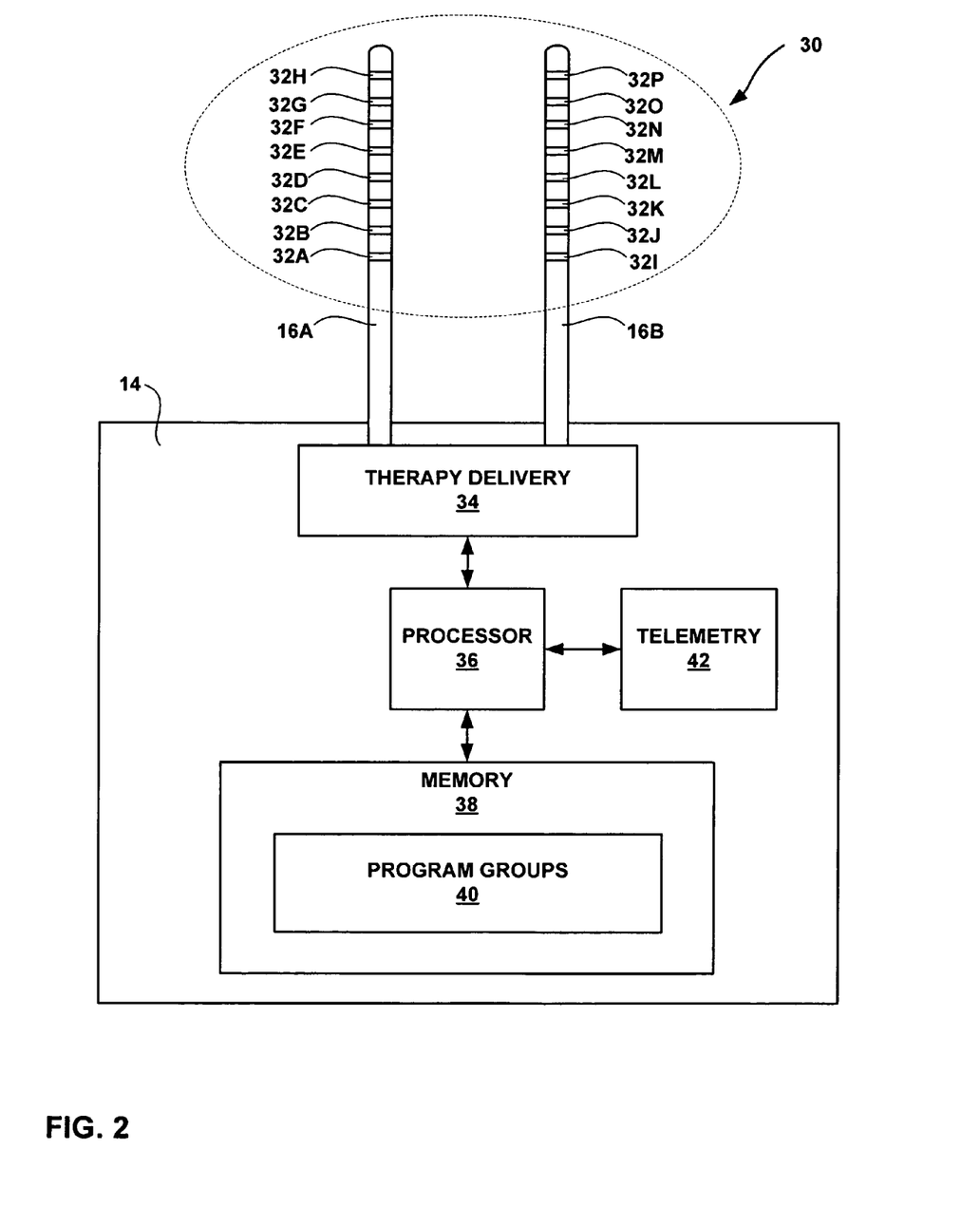
FIG. 2 is a block diagram illustrating an exemplary implantable medical device that delivers neurostimulation therapy to a patient according to a program group.

FIG. 2 is a block diagram illustrating an example configuration of IMD 14. IMD 14 may deliver neurostimulation therapy via electrodes 32A-H of lead 16A and electrodes 32I-P of lead 16B (collectively "electrodes 32"). Electrodes 32 collectively form a set 30 of electrodes implanted within patient 12 (FIG. 1). Electrodes 32 may be ring electrodes. The configuration, type and number of electrodes 32 within set 30 illustrated in FIG. 2 are merely exemplary.

Electrodes 32 are electrically coupled to a therapy delivery circuit 34 via leads 16. Therapy delivery circuit 34 may, for example, include one or more output pulse generators, e.g., capacitive elements and voltage regulators, or current sources, and switches, coupled to a power source such as a battery. Therapy delivery circuit 34 delivers electrical pulses to patient 12 via combination of electrodes 32 from within set 30 that includes two or more active electrodes under the control of a processor 36.

Processor 36 controls therapy delivery circuit 34 to deliver neurostimulation therapy according to a selected program group. Specifically, processor 36 may control circuit 34 to deliver electrical pulses with the amplitudes and widths, and at the rates specified by the one or more constituent programs of a program group. Processor 36 may also control circuit 34 to deliver the pulses via selected combination of electrodes 32 of set 30, as specified by the electrode configurations of the constituent programs. As indicated above, processor 36 may control therapy delivery circuit 34 to deliver pulses according to the constituent programs of a program group in an alternating or interleaved manner. Processor 36 may include a microprocessor, a controller, a digital signal processor (DSP), an application specific integrated circuit (ASIC), an field programmable gate array (FPGA), discrete logic circuitry, or the like.

IMD 14 also includes a memory 38. In the illustrated embodiment, memory 38 stores one or more program groups 40 that are available to be selected by processor 36 for delivery of neurostimulation therapy. Memory 38 may also include program instructions that, when executed by processor 36, cause IMD 14 to perform the functions ascribed to IMD 14 herein. Memory 38 may include any volatile, non-volatile, magnetic, optical, or electrical media, such as a random access memory (RAM), read-only memory (ROM), non-volatile RAM (NVRAM), electrically erasable programmable ROM (EEPROM), flash memory, and the like.

IMD 14 also includes a telemetry circuit 42 that allows processor 36 to communicate with clinician programmer 20. Processor 36 receives programs to test on patient 12 from clinician programmer 20 via telemetry circuit 42 during programming by a clinician. Processor 36 further receives program groups 40 automatically generated by clinician programmer 20 from the programmer via telemetry circuit 42, and stores the received program groups 40 within memory 38.

In addition to clinician programmer 20, some embodiments of the invention may include a patient programmer. The patient programmer may communicate with processor 36 of IMD 14 via telemetry circuit 42. Patient 12 may select a current program group, and may also adjust parameter values for the one or more programs of a program group, via a user interface of the patient programmer and telemetric communication between the programmer and IMD 14. Although described herein with reference to embodiments in which IMD 14 stores the plurality of program groups 40 available for selection and delivery to patient 12, the invention is not so limited. In some embodiments, the patient programmer may receive and store the plurality of program groups 40 from clinician programmer 20, and transmit a selected one of the program groups to IMD 14.

Figure 3:
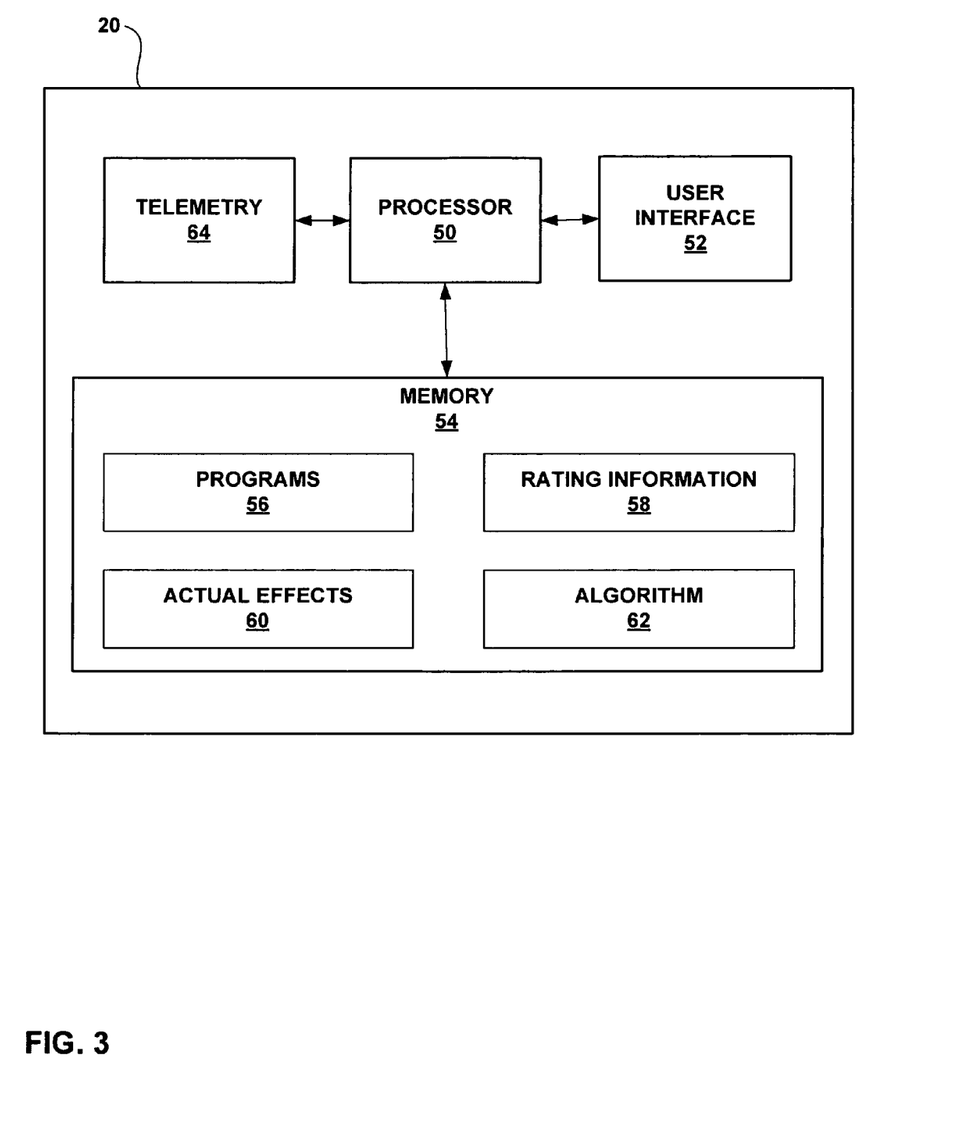
FIG. 3 is a block diagram illustrating an exemplary programming device that automatically generates program groups according to the invention.

FIG. 3 is a block diagram illustrating an example configuration of clinician programmer 20. A clinician, and in some cases patient 12, may interact with a processor 50 via a user interface 52 in order to program neurostimulation therapy for patient 12 as described herein. User interface 52 may include display 22 and keypad 24 (FIG. 1), and may also include a touch screen or peripheral pointing devices as described above. Processor 50 may also provide a graphical user interface (GUI) to facilitate interaction with the clinician. Processor 50 may include a microprocessor, a controller, a DSP, an ASIC, an FPGA, discrete logic circuitry, or the like.

Clinician programmer 20 also includes a memory 54. In some embodiments, memory 54 includes program instructions that, when executed by processor 50, cause clinician programmer 20 to perform the functions ascribed to clinician programmer 20 herein. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

As illustrated in FIG. 3, memory 54 stores information describing programs 56 tested on patient 12, as well as rating information 58 and actual effects 60 recorded for each of the tested programs. In response to input received from a user, e.g., the clinician or patient 12, via user interface 52, processor 50 may control IMD 14 to deliver neurostimulation therapy according to one of programs 56 via telemetry circuitry 64. The user may specify, e.g., create, the program via the user interface. In other embodiments, processor 50 may automatically control testing of a plurality of programs, and in some embodiments may automatically generate the plurality of programs, according to an automated or semi-automated testing routine. In either case, in response to delivery of stimulation according to a program by IMD 14, processor 50 may receive rating information 58 and information describing actual effects 60 for the tested program from the user via user interface 52, and store the information within memory 54. Processor 50 may store the rating and actual effect information for each tested program in association with information describing the program, e.g., in a data structure such as a table, within memory 54.

Processor 50 may automatically generate program groups 40 (FIG. 2) from programs 56, e.g., in response to a command from a user received via user interface 52. Processor 50 may receive target therapy information from the user that includes a plurality of target therapy effects via the user interface. The target therapy information may also include a desired number of program groups. Although not illustrated in FIG. 3, processor 50 may store the target therapy information in memory 54.

Processor 50 may automatically generate program groups 40 from programs 56 based on the rating information for the programs and a comparison of the actual effects for the programs to the target effects specified in the target therapy information, using any of the techniques that will described in greater detail below. Where indicated by the user via user interface, e.g., as part of target therapy data, processor 50 may automatically generate the target number of program groups.

In some embodiments, processor 50 applies an algorithm 62 stored in memory 54 to facilitate automatic generation of program groups. The inputs to the algorithm may include rating information, which may include values for one or more metrics, for an individual tested program or a program group. The inputs to the algorithm may additionally or alternatively include one or more actual therapy effects, and one or more target therapy effects for an individual tested program or a program group. The output of the algorithm may be a score, either for an individual program, or a program group.

Using algorithm 62, processor 50 may synthesize disparate types of information for a plurality of programs or groups into a single score for each program or group to facilitate comparisons and selections by the processor. For example, in some embodiments, processor 50 may determine an overall metric value based on a plurality of metric values recorded as rating information. Where the metric values are numeric values on a scale, such as subjective efficacy or side effect ratings from one to ten, the overall value may be an average. Processor 50 may convert other metric values, such as a power consumption value or therapeutic amplitude range, to numeric values on a common scale for the purpose of determining an overall metric value. Processor 50 may apply weighting values, which may be determined based on user input received via user interface 52, to the metric values prior to determining the overall metric value.

In some embodiments, processor 50 may apply algorithm 62 to similarly synthesize a comparison of actual and target therapy effects with one or more rating information metric values. For example, processor 50 may compare the areas of the body of patient 12 at which a program or group actually produced paresthesia to target paresthesia area, and determine a numeric value based on the comparison. Processor 50 may average or otherwise combine that numeric value with an overall value or individual values for rating information metrics to determine an overall score for a program or group. Processor 50 may apply weighting values, which may be determined based on user input received via user interface 52, to the metric values and comparison value, e.g., a user may select whether rating information, or paresthesia or symptom coverage, should be a more important factor in determining an overall score for a program or program group.

Program groups 40 automatically generated by processor 50 from among programs 56 tested on patient 12 may be transmitted to IMD 14 via telemetry circuit 64. The program groups may also be stored in memory 54, along with the programs, target therapy information, rating information, and actual effect information, as part of a record for patient 12.

Figure 4:
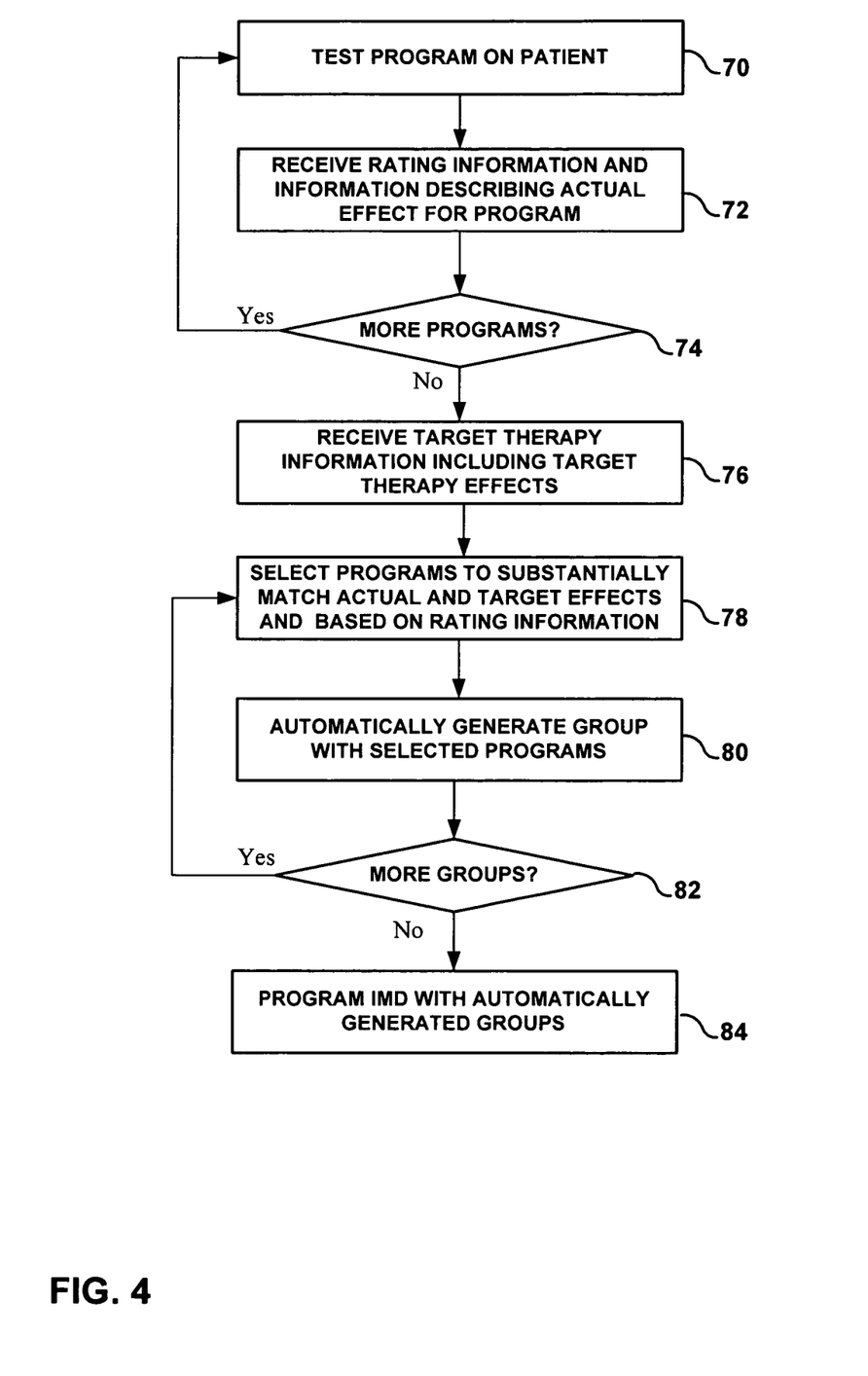
FIG. 4 is a flow diagram illustrating an example method for automatically generating a plurality of program groups.

FIG. 4 is a flow diagram illustrating an example method for automatically generating a plurality of program groups, which may be employed by clinician programmer 20. According to the example method, programmer 20 tests a program 56 on a patient by directing IMD 14 to deliver stimulation to the patient according to the program (70). Programmer 20 receives rating information 58 and information describing the actual therapy effects 60 of the tested program, e.g., from a clinician or patient 12 via user interface 52 of programmer 20 (72). Programmer 20 may continue to test new programs and receive information for the programs (70,72) as directed by a user and/or automated or semi-automated testing routine (74).

Programmer 20 also receives target therapy information that includes one or more target therapy effects, which may occur after a plurality of programs have been tested, as illustrated in FIG. 4 (76). When a plurality of programs have been tested and the target therapy information has been received, programmer 20 selects one or more programs such that their actual effects substantially match or address the target therapy effects based on the rating information (78). For example, if the target therapy information indicates that the user desires a program group that provides paresthesia in the foot and thigh, programmer may select the most highly rated program according to the rating information which has an actual effect of paresthesia in the foot, and the most highly rated program according to the rating information which has an actual effect of paresthesia in the thigh. Programmer 20 may sort the tested programs into lists or the like according to actual effects, rank the lists according to rating information, and select a program from each list address the target therapy effects. Programmer 20 automatically generates a program group with the selected programs (80).

Programmer 20 may continue to select programs and automatically generate groups (78,80), e.g., in a decreasing order with respect to the rating information, until a desired number of program groups substantially addressing the target therapy effects has been generated (82). In some embodiments, as discussed above, the target therapy information received from the user includes a target number of groups, and programmer 20 generates the target number of groups. When the desired number of groups have been generated, programmer 20 programs IMD 14 with the automatically generated groups (84).

Figure 5:
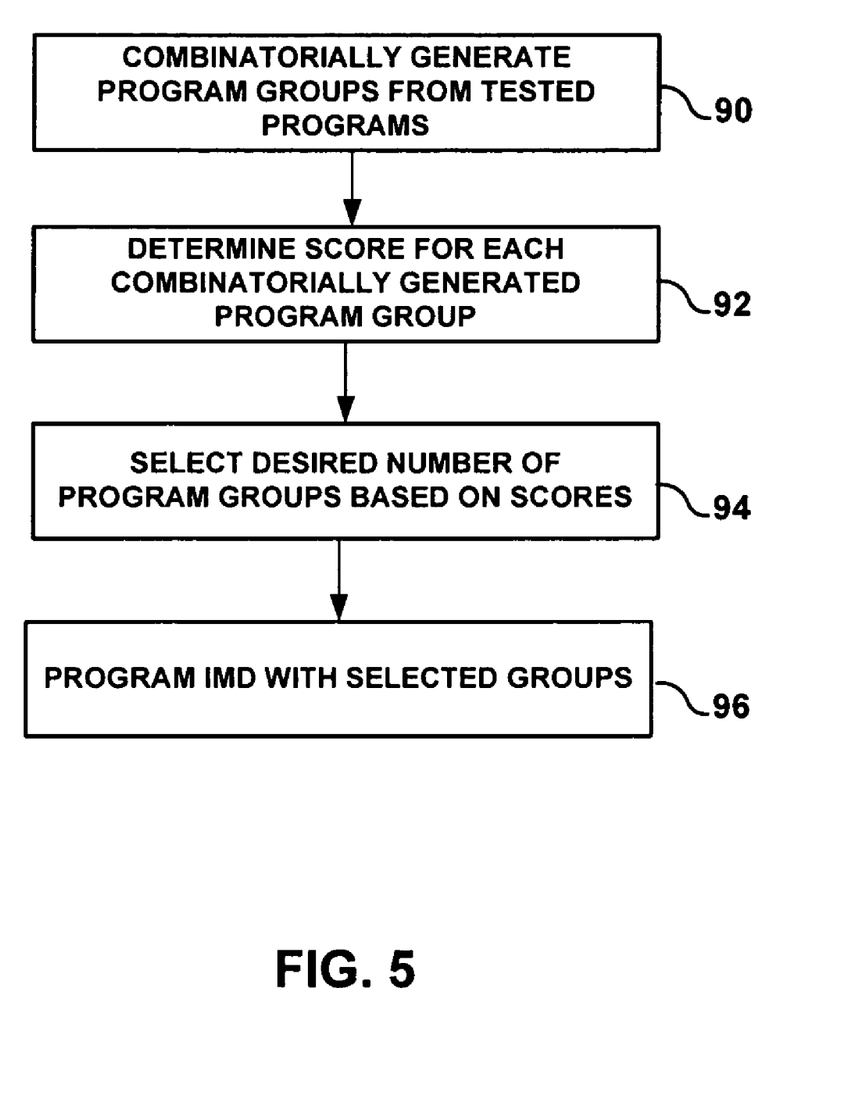
FIG. 5 is a flow diagram illustrating another example method for automatically generating a plurality of program groups.

FIG. 5 is a flow diagram illustrating another example method for automatically generating a plurality of program groups, which may be applied by clinician programmer 20. Programmer 20 may test a plurality of programs, and record rating and actual effect information for each of the tested programs, as described above with reference to FIG. 4 (70-74). Programmer 20 then combinatorially generates program groups from the tested programs, and determines a score for each of the combinatorially generated programs (90,92).

For example, programmer 20 may generate all or some possible combinations of programs whose actual effects address one or more of the target therapy effects, e.g., may generate all possible combinations of programs where one program is selected from each of a plurality of lists into which programs are sorted according to actual effects. In such embodiments, programmer 20 may apply algorithm 62 to determine a score for each group by adding, averaging or otherwise combining rating information values, e.g., values for a plurality of metrics for each of the plurality of programs. In other embodiments, programmer 20 may generate all or some of the possible combinations of tested programs without regard to whether the actual effects of the combined program substantially match the target therapy effects. In such embodiments, programmer may apply algorithm 62 to combine rating information values with values representing a determination of the extent to which the actual effects of the programs address the target effects, in order to determine an overall score for each program group. As part of the determination of an overall score for each program group, programmer 20 may apply weightings to various rating metrics, rating information as a whole, and/or to the comparison of target and actual effects. The weightings may be determined based on input received from a user.

In either case, programmer 20 selects a desired number of the combinatorially generated program groups based on the overall scores to be the automatically generated program groups (94). For example, programmer 20 may select the N program groups with the highest overall scores. Programmer 20 programs IMD 14 with the selected program groups (96).

Figure 6:
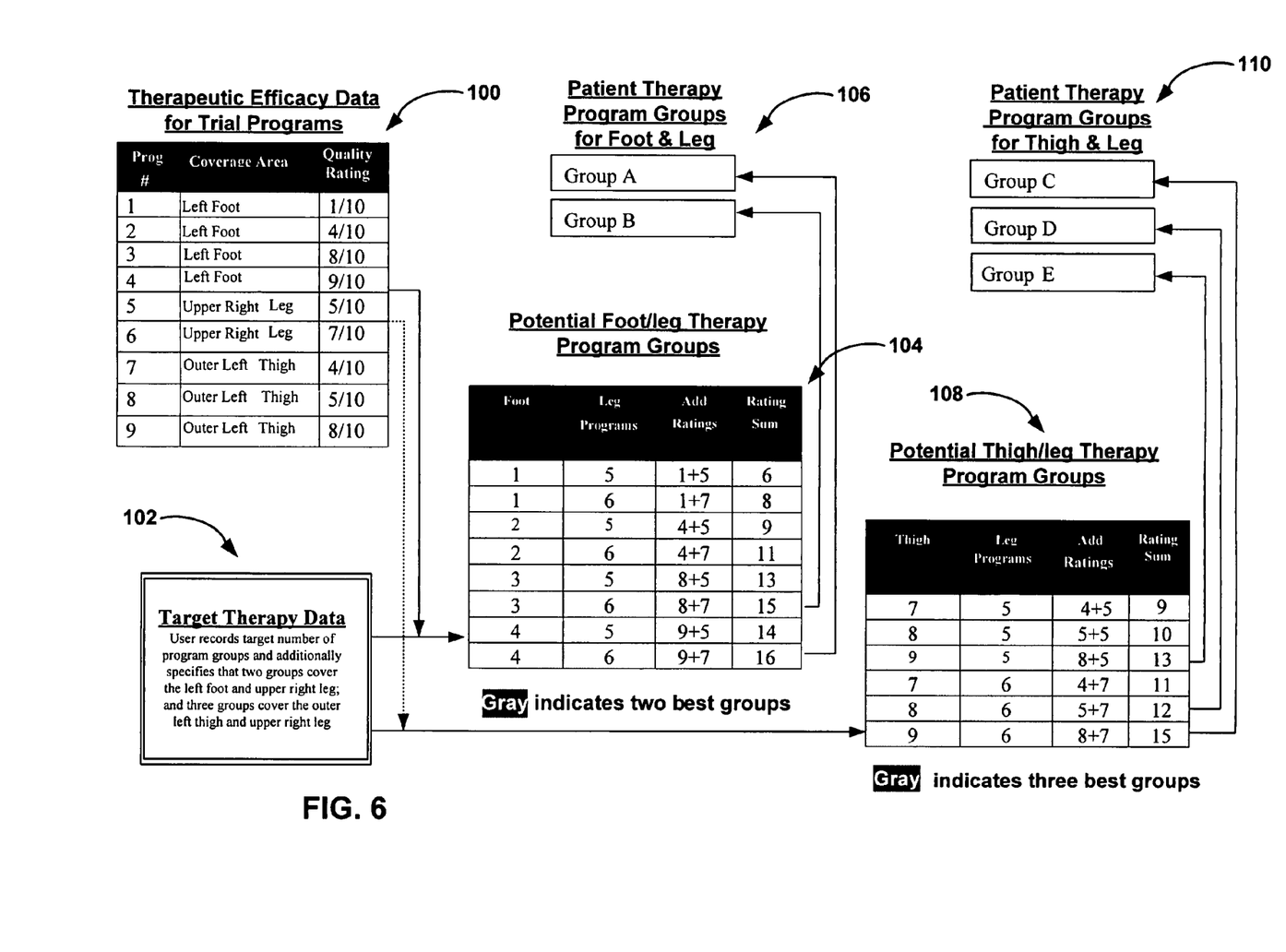
FIG. 6 is a conceptual flow diagram illustrating application of the example method of FIG. 5 according to one embodiment.

FIG. 6 is a conceptual flow diagram illustrating application of the example method of FIG. 5 according to one embodiment. In the example of FIG. 6, programmer 20 has tested and recording information for nine programs (100). The recorded actual effect information includes indication of paresthesia coverage area, such as left foot, upper right leg, and outer left leg. The recorded rating information is a single subjective quality score received from the clinician or patient 12 as a number within the range from 1 to 10.

Programmer 20 has also received target therapy information (102). The target therapy information indicates that the user desires two program groups that cover the left foot and upper right leg, and three program groups that cover the outer left thigh and upper right leg. Programmer 20 then combinatorially generates all possible combinations of the programs that cover the foot with the programs that cover the upper right leg, and applies algorithm 62 to determine the sum of the quality ratings for the constituent programs of each of the combinatorially generated program groups as an overall score for each of the groups (104). Programmer 20 selects the target number, i.e., two, of the program groups that have the highest overall scores (106).

Similarly, programmer 20 combinatorially generates all possible combinations of the programs that cover the outer left thigh with the programs that cover the upper right leg, and applies algorithm 62 to determine the sum of the quality ratings for the constituent programs of each of the combinatorially generated program groups as an overall score for each of the groups (108). Programmer 20 selects the target number, i.e., three, of the program groups that have the highest overall scores (110). Programmer 20 may then program IMD 14 with the selected groups.

Figure 7:
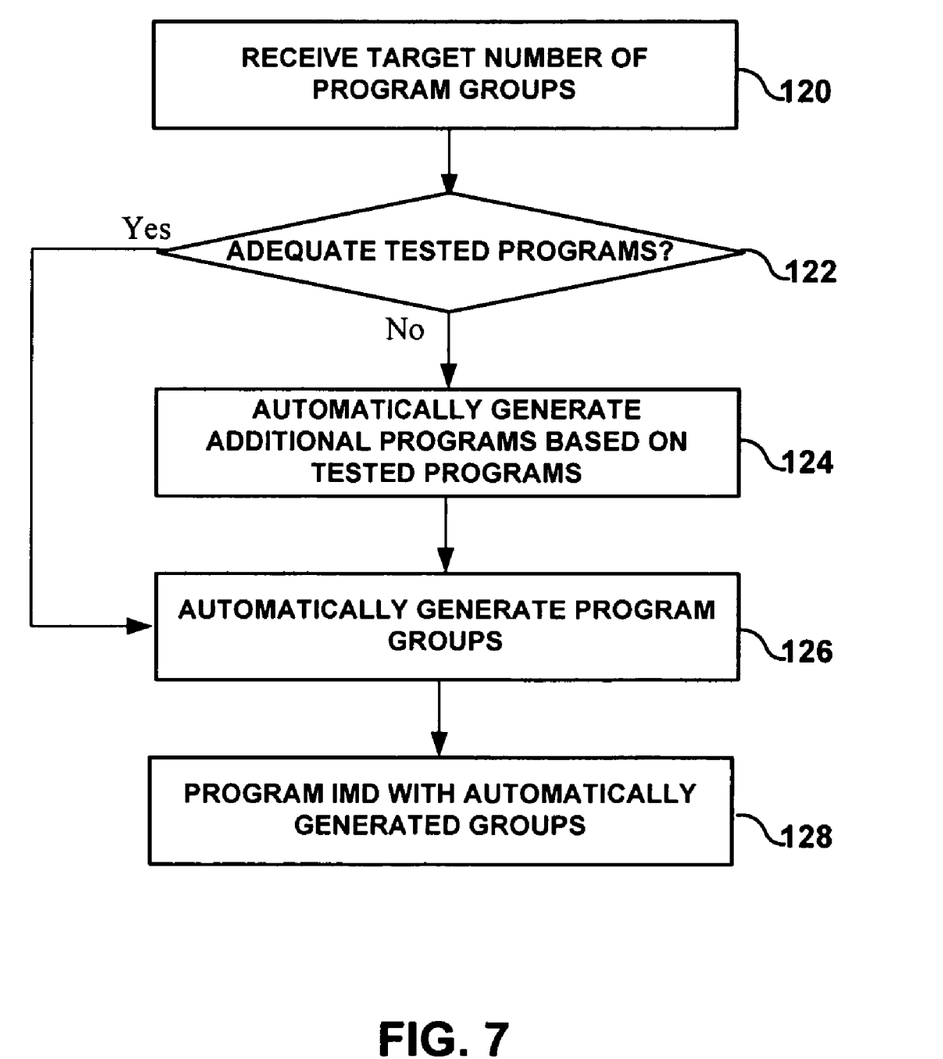
FIG. 7 is a flow diagram illustrating an example method for automatically generating programs to facilitate automatic generation of program groups.

FIG. 7 is a flow diagram illustrating an example method for automatically generating programs to facilitate automatic generation of program groups, which may be employed by programmer 20. Programmer 20 receives a target number of program groups, e.g., from a user, as described above (120). Programmer 20 then determines whether an adequate number of programs have been tested to complete the target number of groups (122). If an adequate number of programs have been tested, programmer 20 automatically generates the desired number of program groups using any of the techniques described herein (126). Programmer 20 may program IMD 14 with the automatically generated program groups (128).

However, if programmer 20 determines that an inadequate number of programs have been tested to generate the target number of program groups, programmer 20 may automatically generate additional programs based on the tested programs until an adequate number of programs are available for automatic group generation (124). Programmer 20 may determine that the overall number of tested programs is inadequate, in which case programmer 20 may generate additional programs from any one or more of the tested programs. Additionally or alternatively, programmer 20 may determine that there is an inadequate number of programs with a specific actual effect to generate the desired number of programs with the desired target effects. In such embodiments, programmer may generate additional programs from one or more tested programs that provided the particular actual effect.

Programmer 20 may automatically generate an additional program from a tested program by generating a copy of the tested program with one of the program parameters modified relative to the tested program. For example, programmer 20 may generate a copy of a tested program with the electrode configuration of the additional program modified relative to the electrode configuration of the tested program. The modification of the electrode configuration may be relatively minor. In some embodiments, programmer 20 may apply one or more rules to the tested program to generate one or more different additional programs. Each of the rules may define a respective electrode configuration modification based on, as examples, the proximity of active electrodes to each other, the proximity of inactive electrodes to active electrodes, or the number of active electrodes.

In general, the rules include at least one of adding an active electrode, removing an active electrode, or changing the location of an active electrode. For example, a rule may specify removal of a cathode that is proximate or adjacent to another cathode, or removal of an anode if there is more than one anode. As other examples, a rule may specify adding an anode or cathode near an existing cathode, or adding an anode near an existing anode. As a further example, a rule may specify moving an anode to a proximate or adjacent inactive electrode. Some of the rules may specify more than one modification, e.g., more than one addition, removal, or movement of an active electrode. Further details regarding various techniques that may be used to generate additional programs from tested programs by modifying electrode configurations may be found in U.S. patent application Ser. No. 11/402,657, by Goetz et al., which is entitled "RULE-BASED STIMULATION PROGRAM SEARCH," and the entire content of which is incorporated herein by reference.

Further, the invention is not limited to embodiments in which programmer 20 generates additional programs by modification of electrode configurations. Programmer 20 may generate additional programs by modifying any one or more of the parameters of a tested program. For example, programmer 20 may modify amplitudes, pulse widths, pulse rates, or pulse morphology.

One skilled in the art will appreciate that various modifications may be made to the described embodiments without departing from the scope of the invention. For example, although program groups are described herein as stored in IMD 14, the invention is not so limited. In some embodiments, the program groups may be stored in the form of a computer-readable medium, such as a read only memory, CD-ROM, magnetic storage medium, and the like. In some embodiments, system 10 includes a patient programmer that patient 12 may use to control delivery of therapy by IMD 14. Patient 12 may activate or adjust delivery of therapy by IMD 14, and may select from among a plurality of program groups used by IMD 14 to deliver neurostimulation therapy via the patient programmer. In some embodiments, the patient programmer stores the program groups used by IMD 14, and transmits a selected program to IMD 14 via device telemetry. In some embodiments, system 10 is a radio-frequency (RF) neurostimulation system, wherein IMD 14 receives both programs of a program group and operating power from the patient programmer.

Although described herein primarily in the context of spinal cord stimulation (SCS) to treat pain, the invention may be used to automatically generate program groups for any type of neurostimulation. For example, in some embodiments, an IMD may deliver neurostimulation to the brain to treat any of a variety of disorders or symptoms, such as tremor, Parkinson's disease, epilepsy, or psychological disorders, or to the urological or gastrointestinal system to treat symptoms or disorders such as gastroparesis, obesity or incontinence. In general, the rating metrics, and actual and target therapy effects for different types of neurostimulation may be different than those described herein. For example, for brain stimulation, target and actual effects may be symptoms, such as tremor, and side effects may include side effects associated with brain stimulation, such as laughter or speech or other neurological function impairment.

Further, although described herein in the context of implantable medical device and implanted electrode sets, the invention is not so limited. For example, an electrode set may be external to a patient, e.g., the electrodes may be placed on the skin of the patient, and used to deliver transcutaneous electrical nerve stimulation (TENS) to the patient.

Additionally, although automatic generation of program groups according to the invention has been described herein as being performed by a single clinician programmer 20, the invention is not so limited. Other computing devices, or other programmers, such as a patient programmer, may automatically generate program groups using any of the techniques described herein. Further, the operations and memory described herein as being performed and located in a single device may be performed and located in a plurality of devices, which may communicate via any of a variety of wired or wireless networks.

Also, although described primarily in the context of embodiments in which rating information and information describing actual effects is collected as a program is tested in a clinic setting, the invention is not so limited. In some embodiments, programmer 20 may additionally or alternatively receive one or both of rating information or information describing actual effects for a program that was collected during use of the program outside of a clinic setting, e.g., at the discretion of patient 12. The program may have been used alone, or as part of a program group. Programmer 20 may receive such information from IMD 14 or a patient programmer used by patient 12 to interact with IMD 14. In such embodiments, rating information may include the various metrics described above, and may also include one or more metrics relating to the extent of use of the program by patient. Further, programmer 20 may use rating information and information describing actual effects for a program tested previously, e.g., during one or more previous clinic session, which may be retrieved from any memory within or accessible by programmer.

As described above, a user may in some embodiments provide input indicating target paresthesia areas and the area or areas covered by a program as that program is tested. One suitable method to ascertain the paresthesia coverage area is to offer a drop-down text list of body parts to the patient during trial program evaluation. Another suitable method is to provide a nondescript yet partitioned drawing of a human body as part of a graphical user interface, which the user interacts with to indicate affected coverage location during evaluation of a trial program. Other methods, such as shading or drawing paresthesia areas on a representation of the human body, are within the scope of this disclosure.

Multiple tested programs might affect the same coverage location on the body; however, it is likely that the metric values, such as a quality rating, would differ between the multiple tested programs. If all tested programs are rated by a user for their therapeutic efficacy with a quality rating upon evaluation on a patient, the tested programs may be ranked according to their therapeutic effectiveness for a particular coverage area using the quality rating. For example, the quality rating may be expressed as a percentage, as a value on a numerical scale, or as a collection of stars.

Battery longevity may also be used as a rating information metric value, or to break a tie in quality rating between two otherwise comparable tested programs. Using battery longevity as a rating metric is convenient because it does not require that a trial program actually be tested on a patient before assigning it a metric value.

Not all rating metrics need be positive. Extraneous coverage is generally considered disadvantageous, so a large area of unwanted coverage could produce a negative metric. The negative scores could be ranked comparably to positive scores during a program selection or ranking process however, lower negative scores would correspond to higher quality ratings.

An alternate approach would set a cutoff point for any one or more of the metrics, and any tested program with a score less than a specified threshold for the metric would be automatically eliminated from consideration, i.e., selection for inclusion in automatically generated program groups. For example, an extraneous coverage metric value could be limited to −5 or greater. If a program received an extraneous coverage score of −6, it would be eliminated based on the specified rating threshold.

As discussed above, embodiments of the invention may apply an algorithm to determine an overall score for a program or group based on a plurality of rating metrics and a comparison of actual effects to target therapy effects, e.g., actual coverage area to desired paresthesia coverage area. The following is another example illustrating an algorithm that may be used to provide an overall score for combinatorially generated groups, and that considers extraneous paresthesia coverage.

For each combinatorially generated group, the following factors may be calculated according to the example:

Good Coverage—The extent to which the target paresthesia coverage areas are covered by the actual paresthesia areas resulting from delivery of the programs of the group.

Bad Coverage—The areas that are covered by the group that are not part of the target paresthesia areas.

Min Goodness—The lowest quality rating value of the programs used for the group, which may be a overall value determine based on values of a plurality of rating information metrics.

Max Goodness—The highest quality rating value of the programs used for the combination, which may be a overall value determine based on values of a plurality of rating information metrics.

Then, a programmer or the like may determine an overall score for each group using weighting factors (K1, K2, K3, and K4), which may be determined based on user input, as described above:

Overall Rating=($K1$)(Good Coverage)−($K2$)(Bad Coverage)+($K3$)(Max Goodness)+($K3$)(Min Goodness)

These and other embodiments are within the scope of the following claims.

The invention claimed is:

1. A method comprising:
   for each of a plurality of neurostimulation programs previously tested on a patient, receiving rating information and information describing at least one actual effect resulting from delivery of neurostimulation therapy according to the program;
   receiving target therapy information from a user for a subsequent neurostimulation therapy session that describes a plurality of desired target therapy effects that the user desires to address in the subsequent neurostimulation therapy session;
   in response to receiving the target therapy information from the user, automatically comparing the actual effects for the previously tested programs to the desired target therapy effects that the user desires to address in the subsequent neurostimulation therapy session; and
   automatically generating a plurality of program groups based on the rating information and the comparison, each of the program groups including a different subset of the neurostimulation programs tested on the patient, wherein each of the program groups include two or more of the neurostimulation programs tested on the patient.

2. The method of claim 1, wherein receiving target therapy information that describes a plurality of desired target therapy effects comprises receiving target therapy information that describes a plurality of target paresthesia coverage areas, and receiving information describing at least one actual effect comprises receiving information describing at least one actual paresthesia coverage area resulting from delivery of neurostimulation therapy according to the program.

3. The method of claim 1, wherein automatically generating a plurality of program groups comprises selecting two or more of the tested programs for each of the program groups based on the rating information and such that the actual effects of the selected two or more programs substantially match the desired target therapy effects.

4. The method of claim 1, wherein automatically generating a plurality of program groups comprises:
   combinatorially generating program groups from the tested programs;
   applying an algorithm to each of the program groups, the algorithm providing a score for each of the program groups based on at least one of the rating information for the constituent programs of the program groups or a comparison of the actual effects for the constituent programs to the desired target therapy effects; and
   selecting the plurality of program groups from among the combinatorially generated program groups based on the scores.

5. The method of claim 1, wherein automatically generating a plurality of program groups comprises applying weightings to the rating information and the comparison of the actual effects to the desired target therapy effects based on user input.

6. The method of claim 1, wherein the rating information for each of the tested programs includes a plurality of metrics, and automatically generating a plurality of program groups based on the rating information comprises determining an overall rating for each of the tested programs by applying weighting values to each of the metrics.

7. The method of claim 6, further comprising selecting the weighting values based on user input.

8. The method of claim 6, wherein the plurality of metrics comprises at least two of an efficacy metric, a side-effects metric, a power consumption metric, or a therapeutic amplitude range metric.

9. The method of claim 1, wherein the target therapy information includes a target number of program groups, and automatically generating a plurality of program groups comprises automatically generating the target number of program groups.

10. The method of claim 9, further comprising:
    determining that a number of the tested programs is insufficient to generate the target number of program groups; and
    in response to the determination, automatically generating additional programs based on the tested programs,
    wherein automatically generating the target number of program groups comprises automatically generating the target number of program groups from the tested programs and the automatically generated programs.

11. The method of claim 10, wherein automatically generating additional programs based on the tested programs comprises generating a copy of at least one of the tested programs with an electrode configuration of the copy modified relative to an electrode configuration of the tested program.

12. A computer-readable storage medium comprising instructions that cause a programmable processor to;
    for each of a plurality of neurostimulation programs previously tested on a patient, receive rating information and information describing at least one actual effect resulting from delivery of neurostimulation therapy according to the program;
    receive target therapy information from a user for a subsequent neurostimulation therapy session that describes a plurality of desired target therapy effects that the user desires to address in the subsequent neurostimulation therapy session;
    automatically compare the actual effects for the previously tested programs to the desired target therapy effects that the user desires to address in the subsequent neurostimulation therapy session in response to receiving the target therapy information from the user; and automatically generate a plurality of program groups based on the rating information and the comparison, each of the program groups including a different subset of the neurostimulation programs tested on the patient, wherein each of the program groups include two or more of the neurostimulation programs tested on the patient.

13. The computer-readable medium of claim 12, wherein the instructions that cause a programmable processor to receive target therapy information that describes a plurality of desired target therapy effects comprise instructions that cause a programmable processor to receive desired target therapy information that describes a plurality of target paresthesia coverage areas, and wherein the instructions that cause a programmable processor to receive at least one actual effect comprise instructions that cause a programmable processor to receive information describing at least one actual paresthesia coverage area resulting from delivery of neurostimulation therapy according to the program.

14. The computer-readable medium of claim 12, wherein the instructions that cause a programmable processor to automatically generate a plurality of program groups comprise instructions that cause a programmable processor to select two or more of the tested programs for each of the program groups based on the rating information and such that the actual effects of the selected two or more programs substantially match the desired target therapy effects.

15. The computer-readable medium of claim 12, wherein the instructions that cause a programmable processor to automatically generate a plurality of program groups comprise instructions that cause a programmable processor to:

combinatorially generate program groups from the tested programs;

apply an algorithm to each of the program groups, the algorithm providing a score for each of the program groups based on at least one of the rating information for the constituent programs of the program groups or a comparison of the actual effects for the constituent programs to the desired target therapy effects; and select the plurality of program groups from among the combinatorially generated program groups based on the scores.

16. The computer-readable medium of claim 12, wherein the instructions that cause a programmable processor to automatically generate a plurality of program groups comprise instructions that cause a programmable processor to apply weightings to the rating information and the comparison of the actual effects to the desired target therapy effects based on user input.

17. The computer-readable medium of claim 12, wherein the rating information for each of the tested programs includes a plurality of metrics, and the instructions that cause a programmable processor to automatically generate a plurality of program groups based on the rating information comprise instructions that cause a programmable processor to determine an overall rating for each of the tested programs by applying weighting values to each of the metrics.

18. The computer-readable medium of claim 17, further comprising instructions that cause a programmable processor to select the weighting values based on user input.

19. The computer-readable medium of claim 17, wherein the plurality of metrics comprises at least two of an efficacy metric, a side-effects metric, a power consumption metric, or a therapeutic amplitude range metric.

20. The computer-readable medium of claim 12, wherein the target therapy information includes a target number of program groups, and the instructions that cause a programmable processor to automatically generate a plurality of program groups comprise instructions that cause a programmable processor to automatically generate the target number of program groups.

21. The computer-readable medium of claim 20, further comprising instructions that cause a programmable processor to:

determine that a number of the tested programs is insufficient to generate the target number of program groups; and in response to the determination, automatically generate additional programs based on the tested programs, wherein the instructions that cause a programmable processor to automatically generate the target number of program groups comprise instructions that cause a programmable processor to automatically generate the target number of program groups from the tested programs and the automatically generated programs.

22. The computer-readable medium of claim 21, wherein the instructions that cause a programmable processor to automatically generate additional programs based on the tested programs comprise instructions that cause a programmable processor to generate a copy of at least one of the tested programs with an electrode configuration of the copy modified relative to an electrode configuration of the tested program.

23. A device comprising:

a user interface; and a processor that for each of a plurality of neurostimulation programs previously tested on a patient, receives rating information and information describing at least one actual effect resulting from delivery of neurostimulation therapy according to the program via the user interlace, receives target therapy information from a user for a subsequent neurostimulation therapy session that describes a plurality of desired target therapy effects that the user desires to address in the subsequent neurostimulation therapy session via the user interface, automatically compares the actual effects for the previously tested programs to the desired target therapy effects that the user desires to address in the subsequent neurostimulation therapy session in response to receiving the target therapy information from the user, and automatically generates a plurality of program groups based on the rating information and the comparison, each of the program groups including a different subset of the neurostimulation programs tested on the patient, wherein each of the program groups includes two or more neurostimulation programs tested on the patient.

24. The device of claim 23, wherein the desired target therapy effects comprise target paresthesia coverage areas, and the at least one actual effect for each of the tested programs comprises at least one actual paresthesia coverage area resulting from delivery of neurostimulation therapy according to the program.

25. The device of claim 23, wherein the processor selects two or more of the tested programs for each of the program groups based on the rating information and such that the actual effects of the selected two or more programs substantially match the desired target therapy effects.

26. The device of claim 23, wherein the processor to combinatorially generates program groups from the tested programs, applies an algorithm to each of the program groups, the algorithm providing a score for each of the program groups based on at least one of the rating information for the constituent programs of the program groups or a comparison of the actual effects for the constituent programs to the desired target therapy effects, and selects the plurality of program groups from among the combinatorially generated program groups based on the scores.

27. The device of claim 23, wherein the processor applies weightings to the rating information and the comparison of the actual effects to the desired target therapy effects based on user input.

28. The device of claim 23, wherein the rating information for each of the tested programs includes a plurality of metrics, and the processor determines an overall rating for each of the tested programs by applying weighting values to each of the metrics.

29. The device of claim 28, wherein the processor selects the weighting values based on user input.

30. The device of claim 28, wherein the plurality of metrics comprises at least two of an efficacy metric, a side-effects metric, a power consumption metric, or a therapeutic amplitude range metric.

31. The device of claim 23, wherein the target therapy information includes a target number of program groups, and the processor automatically generates the target number of program groups.

32. The device of claim 31, wherein the processor determines that a number of the tested programs is insufficient to generate the target number of program groups, in response to the determination, automatically generates additional programs based on the tested programs, automatically generates the target number of program groups from the tested programs and the automatically generated programs.

33. The device of claim 32, wherein the processor automatically generates additional programs by generating a copy of at least one of the tested programs with an electrode configuration of the copy modified relative to an electrode configuration of the tested program.

34. A device comprising:
means for receiving rating information and information describing at least one actual effect resulting from delivery of neurostimulation therapy according to the program for each of a plurality of neurostimulation programs previously tested on a patient;
means for receiving target therapy information from a user for a subsequent neurostimulation therapy session that describes a plurality of desired target therapy effects that the user desires to address in the subsequent neurostimulation therapy session;
means for comparing the actual effects for the previously tested programs to the desired target therapy effects that the user desires to address in the subsequent neurostimulation therapy session in response to receiving target therapy information from the user; and
means for automatically generating a plurality of program groups based on the rating information and the comparison, each of the program groups including a different subset of the neurostimulation programs tested on the patient, wherein each of the program groups includes two or more neurostimulation programs tested on the patient.

* * * * *

UNITED STATES PATENT AND TRADEMARK OFFICE
CERTIFICATE OF CORRECTION

| | | |
|---|---|---|
| PATENT NO. | : 7,774,067 B2 | Page 1 of 1 |
| APPLICATION NO. | : 11/402652 | |
| DATED | : August 10, 2010 | |
| INVENTOR(S) | : Steven M. Goetz et al. | |

It is certified that error appears in the above-identified patent and that said Letters Patent is hereby corrected as shown below:

Col. 18, Line 36: "user interlace" should read --user interface--

Signed and Sealed this
Sixteenth Day of August, 2011

David J. Kappos
*Director of the United States Patent and Trademark Office*